United States Patent [19]
Hahn et al.

[11] Patent Number: 5,405,356
[45] Date of Patent: Apr. 11, 1995

[54] CHILD-BIRTH ASSISTING SYSTEM

[75] Inventors: Soonkap Hahn, Poway; Wei Pan, La Jolla; Ron Yamamoto, San Francisco; Peter M. Lloyd, Oceanside; Mingying Gai, Los Angeles, all of Calif.

[73] Assignee: JCS Biomedical, Inc., Poway, Calif.

[21] Appl. No.: 86,099

[22] Filed: Jun. 30, 1993

[51] Int. Cl.$^6$ .............................................. A61B 17/42
[52] U.S. Cl. ..................................... 606/202; 128/775
[58] Field of Search ....................... 606/119, 201–203; 128/24 R, 24.2, 28, 30, 30.2, 31, 775, 778

[56] References Cited

U.S. PATENT DOCUMENTS

| | | | |
|---|---|---|---|
| Re. 31,158 | 2/1982 | Carter et al. | 128/778 |
| 4,294,261 | 10/1981 | Baker et al. | 606/202 |
| 4,321,929 | 3/1982 | Lemelson et al. | 606/202 |
| 4,873,986 | 10/1989 | Wallace | 128/775 |
| 4,949,730 | 8/1990 | Cobben et al. | 128/775 |

FOREIGN PATENT DOCUMENTS 1800287  4/1970  Germany .............................. 606/119

Primary Examiner—Stephen C. Pellegrino
Assistant Examiner—William Lewis
Attorney, Agent, or Firm—Brown, Martin, Haller & McClain

[57] ABSTRACT

The childbirth-assisting device uses an automatically synchronized expandable pneumatic girdle-to externally augment the secondary force of labor. The pneumatic girdle is fitted around the abdomen of the woman and the girdle is inflated to create a downward pressure on the abdomen when a contraction occurs. The synchronization of the girdle's inflation and the contractions is provided by an electronic controller which receives a signal from an intra-uterine monitor indicating a contraction and causes the girdle to inflate at a certain rate until a preset intra-uterine pressure is attained. Once the intra-uterine pressure reaches the preset pressure, the girdle pressure is maintained until the offset of the contraction is detected, at which time the girdle is deflated.

12 Claims, 3 Drawing Sheets

CHILD-BIRTH ASSISTING SYSTEM

FIELD OF THE INVENTION

The invention generally relates to the field of labor assisting devices, and specifically to a device which simulates the secondary force of labor.

BACKGROUND OF THE INVENTION

A normal labor process is divided into three stages. Among these stages, the first and second stages are the crucial ones which are directly involved in the delivery of fetus. The first stage of labor begins with the onset of rhythmic uterine contraction and ends at the complete dilation of the cervix which is about 10 cm in diameter. The complete dilation of the cervix marks the beginning of the second stage of labor which ends immediately after the birth of the fetus. The third stage of labor extends from the birth of the baby to the complete expulsion of the placenta. The labor progress is driven by two types of labor forces. The primary force is produced by the involuntary contractions of uterine muscle. The secondary force is produced by the increase of intra-abdominal pressure through voluntary contractions of the abdominal muscles and diaphragm. These forces cause an increase of intrauterine pressure to provide a critical expulsion force on fetus.

As often seen in clinical practice, systemic analgesic drugs, epidural anesthesia and long duration of exhaustive labor all can lead to the weakening of secondary force, and sequentially to delayed labor duration or even dystocia (arrest of labor). Numerous clinical studies have correlated a prolonged labor duration and dystocia with many undesirable outcomes, such as higher rate of infant mortality, neonatal seizures and postpartum hemorrhage. To solve these serious problems, clinical instruments (forceps or vacuum suction) or cesarean section are often required to terminate labors. However, both instrumental delivery and cesarean section are far from trouble-free. While a cesarean section is basically safe, it remains a major surgical procedure. Patients who lo give birth by cesarean section are at much greater risk of childbirth-related illness or death than women who deliver vaginally. Also, the average cesarean birth has a length of hospital stay double that of a normal delivery and costs up to three times as much. Instrumental delivery also has limitations and may result in numerous complications including head and facial injuries to fetus. Therefore, it is in the best interest of both mother and fetus to prevent the incidence of prolonged duration of labor or dystocia.

One method of decreasing the incidence of prolonged labor is oxytocin infusion, which is commonly used in clinical practice to increase the primary labor force by directly inducing uterine contraction. Clinical evidence has demonstrated that oxytocin alone can only partially solve the problem of prolonged labor and dystocia associated with epidural anesthesia. However, a high incidence of cesarean section still occurs in patients receiving epidural anesthesia in spite of a high dosage of oxytocin infusion. Furthermore, high doses of oxytocin has been implicated in uterine tetanus and in some adverse neonatal outcomes, including fetal asphyxia.

Devices directed toward assisting in delivery are disclosed in the prior art. In the apparatus of Heidenwolf (U.S. Pat. No. 2,597,637, issued May 20, 1952), an inflatable bladder is held against the woman's upper abdomen by a wide belt. Extending from the bottom of the belt is a pair of straps which, in turn, attaches to straps surrounding the upper thighs. This structure holds the belt down to prevent slippage.

In the birth-assisting pneumatic cuff of Lee (U.S. Pat. No. 5,174,281, issued Dec. 29, 1992), an inflatable bladder fits over and around the woman's abdomen and is manually inflated and deflated in coordination with the patient's voluntary straining during the second stage of labor. This device applies pressure equally to the entire abdomen.

The Chinese patent of Fei Chao (Chinese Patent No. 2198, issued in 1989) teaches an abdominal girdle which has a generally triangular bladder (to match the rough contour of the uterus)which is placed over the patient's abdomen. The bladder is inflated manually in coordination with the woman's contractions to apply a downward pressure on the abdomen, assisting in forcing the fetus downward. While the girdle itself is very effective, the manual control of the inflation/deflation may not be easily accepted by physicians who may be reluctant to rely on a device which could be easily subject to human error with serious consequences.

Related prior art may be seen in the areas of anti-G pressure suits and in inflatable tourniquets and splits. Examples of pressure suits are taught by Crosbie et al. in U.S. Pat. No. 4,534,338, issued Aug. 13, 1985, and Van Patten, U.S. Pat. No. 4,736,731, issued Apr. 12, 1988. These suits inflate in response to changes in the rate of acceleration of an aircraft. Poole, et al. (U.S. Pat. No. 4,531,516, issued Jul. 30, 1985), Manes (U.S. Pat. No. 4,548,198, issued Oct. 22, 1985) and Kitchin et al. (U.S. Pat. No. 4,520,820, issued Jun. 4, 1985) teach inflatable devices for first aid applications. The latter two patents include disclosure of controllers for maintaining constant pressure, however none of these patents addresses synchronization of inflation/deflation as would be required for a labor and delivery-assisting device.

BRIEF SUMMARY OF THE INVENTION

It is an advantage of the present invention to provide a device for assisting in delivery by simulating the secondary force of labor.

It is another advantage of the present invention to provide a childbirth-assisting device which is synchronized with uterine contractions.

Still another advantage of the present invention is to provide a means for preventing prolonged labor while avoiding cesarean section.

In an exemplary embodiment, the childbirth-assisting device uses an automatically synchronized expandable pneumatic girdle to externally augment the secondary force of labor. The pneumatic girdle with a generally triangular bladder (as taught by Fei Chao) is fitted around the abdomen of the woman and the girdle is inflated to create a downward pressure on the abdomen when a contraction occurs. The synchronization of the girdle's inflation and the contractions is provided by a microprocessor-based electronic controller which receives a signal from an intra-uterine monitor indicating a contraction and commands the girdle to inflate at a certain rate until a preset intra-uterine pressure is attained. Once the intra-uterine pressure reaches the preset pressure, the girdle pressure is maintained until the offset of the contraction is detected, at which time the girdle is deflated.

The electronic controller, with programming utilizing rule-based methods, constantly monitors and initiates alarms for hazardous conditions including excessively long contraction periods, paired contractions, skewed contractions and other types of irregular contractions. The controller controls the girdle pressure according the stage of labor and distinguishes between actual and "false" contractions, which may be detected by the intra-uterine monitor when the patient moves.

The childbirth assisting device can potentially be used in both the first stage and the second stage of labor. During the first stage of labor, the device can increase the abdominal pressure, aiding in the effacement of the cervix and hastening the descent of fetus and the cervical dilation process. During the second stage of labor, the device can provide a critical expulsion force for delivery of the fetus.

The childbirth assisting device can efficiently and safely prevent prolonged duration of labor and dystocia due to systemic analgesia, epidural anesthesia, or maternal exhaustion, which can lead to reduction of the cesarean section rate and rate of instrumental delivery. Since weakening of the secondary labor force is particularly common in patients receiving epidural anesthesia, the device can effectively prevent weakening of the secondary labor force under anesthesia, enabling a safer and less painful delivery.

By reinforcing the secondary labor force, the childbirth assisting device can further reduce the rate of cesarean section associated with dystocia and also lower the dosage of oxytocin. Functioning through different mechanisms, the device can be used to complement the benefits of oxytocin in clinical practice.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which.

DETAILED DESCRIPTION OF A PREFERRED EMBODIMENT

Figure 1:
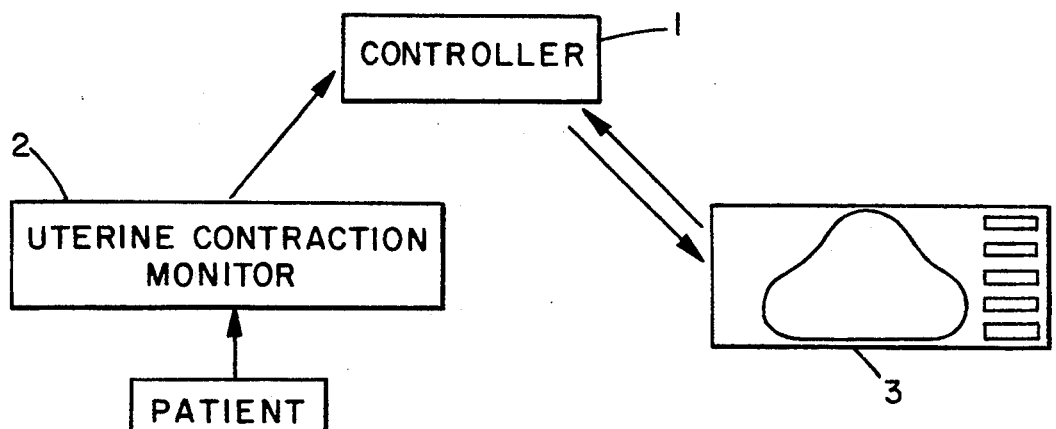
FIG. 1 is a block diagram of function of the childbirth assisting device of the present invention.

FIG. 1 is a block diagram of the childbirth assisting device including a patient and a uterine contraction monitor 2. A closed loop system uses patient response and rule-based decision making methods to achieve operator specified responses. The inventive device is a pneumatic closed loop system which is composed of an abdominal girdle 3 and a controller 1. The controller 1 possesses five main functions:

1. Receiving the uterine activity data from the uterine contraction monitor 2 and detecting the onset and offset of contractions.
2. Synchronizing the girdle pressure with the contraction, increasing the girdle pressure at the onset of contraction and decreasing it at the offset of contraction.
3. Adjusting the girdle pressure automatically to obtain the intrauterine pressure at a preset level.
4. Displaying information, including the girdle pressure.
5. Setting an alarm or alert system for abnormal situations.

The uterine contraction activity can be monitored either internally or externally. Internal pressure monitoring provides the most accurate assessment of uterine activity by allowing pressure changes in the uterus to be transmitted via a fluid-filled catheter to a strain gauge transducer. This produces quantitative readings of the duration, frequency, and amplitude of the uterine contraction, as well as the baseline tone of the uterus. An external tocodynamometry, which can be applied easily at any stage of labor, provides a non-invasive method of assessing uterine contractions. This yields a fairly reliable estimate of frequency of the contractions but a less accurate reading of the contraction intensity than an intrauterine catheter. The actual amplitude of the contraction cannot be measured by this method. In the preferred embodiment, the controller I receives the uterine activity data from an internal pressure monitor 2. The internal pressure monitor provides the accurate intrauterine activity data to the controller, which are necessary for improving the safety and efficiency of inventive device.

Figure 2:
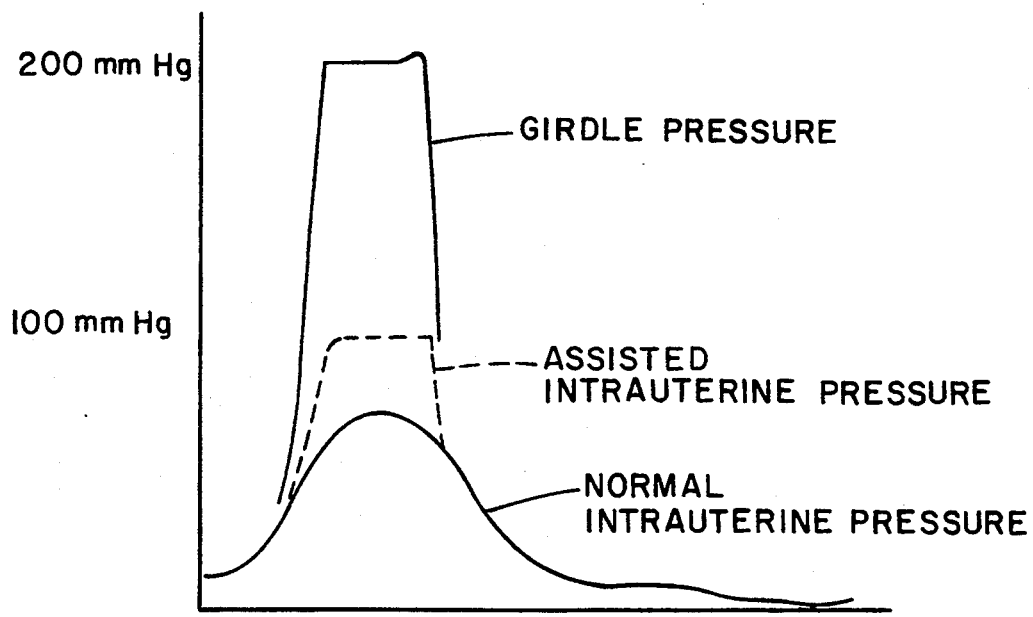
FIG. 2 is a plot of pressure versus contraction duration.

The normal uterine contraction curve is bell-shaped, as shown in FIG. 2, with the descending limb returning to the same basal level as preceded the ascending limb. At the beginning of the first stage of labor with cervical dilation up to 3 cm, an average increase in maximum uterine pressure above basal level is about 20–30 mmHg while at the active phase, with cervical dilation from 3 cm to 10 cm and the second stage of labor, it is in the range of 40–50 mmHg. Contraction frequency also increases from two to three per 10 minutes to four to five per 10 minutes at the end of labor. On slow rise of uterine pressure, the controller evaluates the uterine activity data and determines the onset of contraction. Once the controller 1 detects the onset of contraction, the girdle pressure will be increased. Determining the onset of contraction is somewhat arbitrary. This invention may not be recommended for use during the early first stage of labor including the early active phase (cervical dilation up to 6–7 cm). In the preferred embodiment, the onset of contraction is set at 15–20 mmHg above the basal level. At the onset of contraction, the girdle pressure is increased at the preset rate until the preset intrauterine pressure is obtained. Once the intrauterine pressure reaches the preset pressure, the girdle pressure will be maintained to obtain a constant intrauterine pressure. The offset of contraction can be detected when the girdle pressure increases sharply, as shown in FIG. 2. The girdle pressure will be released upon detection of the offset of contraction.

Figure 3:
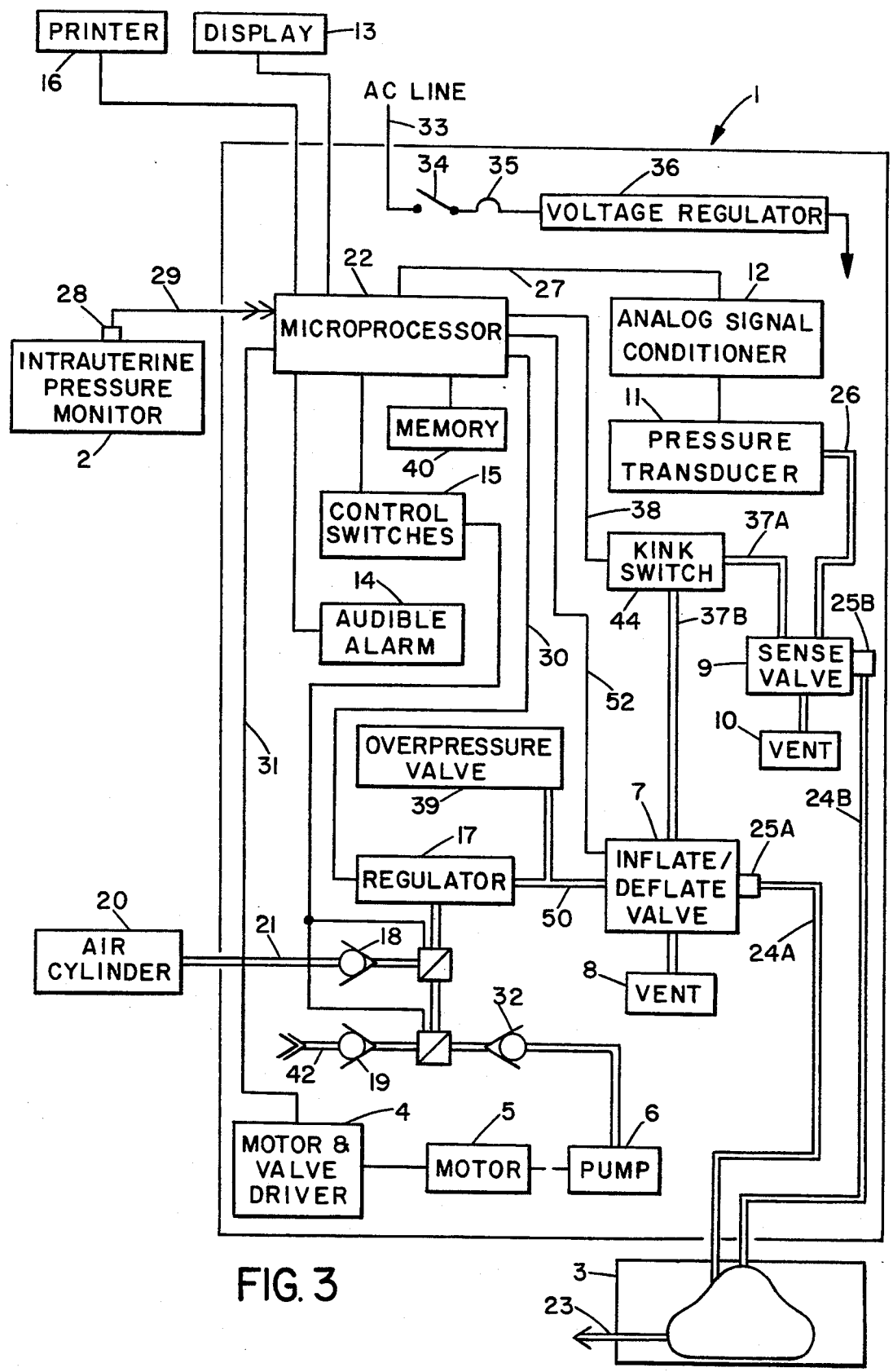
FIG. 3 is a block diagram of the components of the invention.
Figure 4:
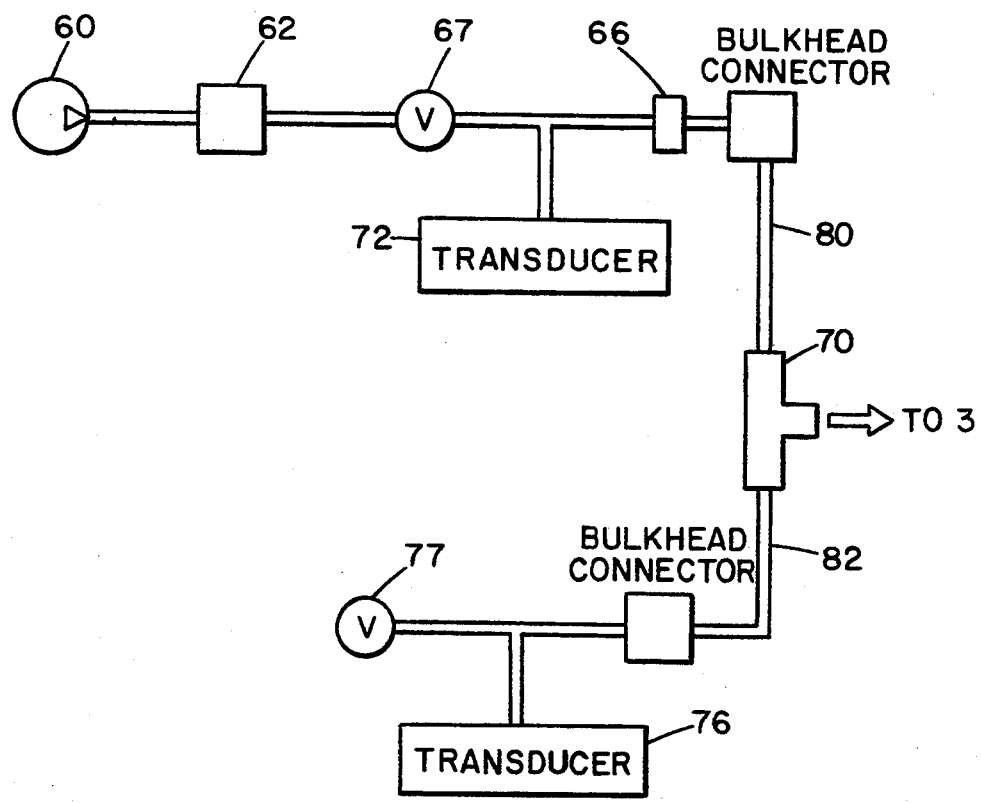
FIG. 4 is another block diagram of the components.

FIG. 3 is a block diagram of automatic labor assisting device, showing the details of the controller 1 and the girdle 3 according to the present invention. Within controller 1, a pressure sensing means, including pressure transducer 11 and analog signal conditioner 12, produces a signal which is fed into the microprocessor 22. The signal is quantized in a 12 bit analog-to-digital converter within the microprocessor 22. A display means, which includes a memory and signal processing circuitry within the microprocessor 22 and display 13, produces a pressure display of the girdle's internal pressure. A memory 40 within the controller provides storage for control parameters and a library of diagnostic information, which is described below in more detail. An inflatable girdle 3 is shown connected via tubing 24A and 24B to the controller I at coupling 25A and 25B. Coupling 25B is connected via valve 9 and pressure line 26 to pressure transducer 11. A signal representing the pressure measured by the pressure transducer 11 and analog signal conditioner 12 is applied via electrical line 27 to microprocessor 22. Two of the control switches 15 are used to apply a signal to microprocessor 22 to set a target intrauterine pressure and a maximum girdle pressure. A signal representing intrauterine pressure is applied to microprocessor 22 via connector 28 and electrical line 29.

Microprocessor 22 is programmed to calculate the girdle pressure adjustment proportional to the magnitude of the difference between the intrauterine pressure and the selected target pressure, and produces an output signal on line 30 which indicates the girdle pressure adjustment. A select switch in control switch 15 determines if an external air line via air line 42, an internal replaceable air bottle via connector 21, or an internal motor 5 and pump 6 are to be used to inflate the girdle. Note that all three air paths are isolated from each other via check valves 18, 19 and 32. The motor 5 is turned on and off by the microprocessor 22 via line 31 to a motor and valve driver circuit 4. The pressure to the girdle 3 is controlled by the regulator 17. Valve 7 vents the pressure in girdle 3 via vent 8 for a time determined by microprocessor 22 through line 52.

Power is applied to controller 1 through line 33 via switch 34 and circuit breaker 35. A voltage regulator 36 provides a 5 volt regulated voltage which is used to power the portion of the digital circuit requiring a positive 5 volts. The 12-volt voltage output is also provided for portions of the circuitry such as the valves, pumps and pressure transducer which require 12-volt power supply. Differential pressure switches 44 are connected between lines 37A and 38B. If any obstruction occurs between lines 37A and 37B, switches 44 apply a signal to microprocessor 22 through line 38 to sound an alarm.

The microprocessor 22 utilizes the information and the signals applied to it to control the girdle 3 and to provide information output. Signals applied from microprocessor 22 to the displays 13 and printer 16 include:
Target intrauterine pressure
Maximum girdle pressure
Current intrauterine pressure
Uterine pressure due to primary force
Current girdle pressure
Diagnostic information for doctor
Alarm for whether there is an obstruction (kink).

The microprocessor 22 compares the input signal received from the intrauterine monitor and the girdle pressure sensors against criteria which are stored in the memory 40. These criteria include the various pressure settings, as well as means for identifying the presence of abnormal contractions which may require modification of the operating parameters of the controller or may require removal of the girdle.

Signals are generated to sound alarm 14 whenever alarm conditions are met. The alarm may be silenced if desired via one of the control switches or by pressing an emergency stop button which will deactivate the controller and deflate the girdle. Sense valve 9 is connected between girdle 3 and pressure transducer 11. The sense valve 9 connects the pressure transducer 11 to atmosphere through vent 10 during the girdle start-up sequence in order to correct the pressure transducer zero offset. Overpressure valve 39 is connected to the line 50 between regulator 17 and inflate-deflate valve 7. This is a manually adjustable valve which limits the maximum pressure delivered to the girdle, in the event that all the safeguards in the air regulation line systems fail. In addition, safety valve 23 is designed into the girdle 3 to deflate the girdle in case of extreme overpressure which would endanger the fetus.

Displaying various forms of outputs is an important function of the controller 1. The girdle pressure and the patient information are displayed on the screen.

To detect hazardous conditions or unexpected patient responses, numerous alert and alarm criteria may be optionally implemented within the device control software:

1. Setting a maximum duration at the target intrauterine pressure during the contraction: A normal contraction may last about 60–90 seconds. However, abnormal contractions such as polysystole, skewed contractions and tachysystole may show a longer contraction period due to a slow return to a baseline. This may result in applying the high pressure onto the abdomen over an extended period. To avoid this problem, the maximum duration at the target intrauterine pressure during the contraction will be established at 20–60 seconds.

2. Setting an interval between two cycles of girdle pressure increase: Contraction frequency increases from two to three per 10 minutes to four to five per 10 minutes at the end of labor. Abnormal contractions such as paired contractions show much a shorter interval between two contractions. The use of the labor assisting device in this case may result in applying an excessive force to the abdomen in a short time period. This problem will be solved by setting a minimum interval between two cycles of girdle pressure increase. The minimum interval will be set at 1.5–5 minutes.

3. Setting the target intrauterine pressures at different stages of labor: In normal labor, an average increase in maximum uterine pressure above basal level begins with about 20–30 mmHg at the early first stage of labor and becomes 40–50 mmHg at the active phase and the second stage of labor. This force is mainly produced by the primary and involuntary force. In addition to the primary force, the use of the inventive device will increase the intrauterine pressure further by providing the secondary force. To enhance the safety of the device, the target intrauterine pressures are assessed during various phases of labor. For example, the target intrauterine pressure during the stage of labor with cervical dilation from 3 cm to 8 cm is set at 40–60 mmHg above the baseline while during the active phase with cervical dilation from 8 cm to 10 cm at 60–80 mmHg and the second stage of labor at 80–160 mmHg. The decision of whether the stage of labor is early or active should be made by a physician. Obstetricians also set up the appropriate target intrauterine pressure depending on clinical situations. Any uncontrollable intrauterine pressure increase above the target pressure (15 mmHg higher than the target) will trigger the alarm system and rapidly deflate the girdle.

4. Setting a limit of the girdle pressure at each target intrauterine pressure: This mechanism also prevents any extra force on the abdomen which may result from malfunctions of the device. For example, the limit of the girdle pressure will be set at 150 mmHg during the stage of labor with cervical dilation from 3 cm to 8 cm when the target intrauterine pressure is 40–60 mmHg. The limit will be set at 250 mmHg during the active phase of labor with cervical dilation from 8 cm to 10 cm when the target intrauterine pressure is 60–80 mmHg. The limit will be set at 350 mmHg during the second stage of labor. The girdle pressure above these limits triggers the alarm system and rapidly deflates the girdle. The girdle may also be implemented with its own safety valve which be blown if the pressure exceeds 350 mmHg.

5. Filtering the false contractions: The movement of patient sometimes generates the sudden rise of intrauterine pressure. This can be filtered by evaluating the rate of intrauterine pressure increase, defined as a derivative, $dP/dt$, where P=intrauterine pressure and t=time, and comparing with a normal range of the rate. Any contractions with the rate of intrauterine pressure higher than the normal range will be treated as false contractions and will not trigger the inflation of the girdle.

For the safe use of the childbirth assisting device, several abnormal clinical situations have been considered. The criteria for each of these situations is stored within a library in the controller's memory 40 and the contraction data is compared against these criteria to determine whether the abnormal condition is present. If so, an alarm condition is initiated and an output is provided to indicate the presence of the abnormal condition. The following situations are included in the library of abnormal conditions:

1. Hypotonia/Hypocontractility:
   When contractions are less than 25 to 30 mmHg at their peak, or recur less frequently than every five minutes in the active phase of labor and last less than 45 seconds, hypocontractility is present, even if it is accompanied by progress in labor. The decreased uterine activity may be due to the abnormal contraction, hypotonia, or the artifact from the presence of air in the internal monitoring system. In both cases, the use of the device may not cause safety problems. However, since the device will not allow the girdle pressure to exceed the safety limit, the alarm system will be on before the target intrauterine pressure is obtained. The correction should be made upon a proper diagnosis of the above problems. The presence of air in the internal monitoring system can be corrected easily and device can be restarted.

2. Polysystole:
   Polysystole is a common abnormal uterine waveform that is characterized by a single contraction with two or more peaks. It is also described as two or more contractions in juxtaposition without full return to the baseline between each. This could be determined by software and if the situation meets the alarm criteria set in the above section, the girdle should deflate and a physician should be informed.

3. Discoordinate uterine activity:
   The constancy of the intervals between uterine contractions determines the degree of coordination or rhythm of uterine activity. When a marked variation occurs from contraction to contraction, the resultant pattern is termed "discoordinate labor". Because contractions may be generated from alternate uterine cornua as well as from other sites, frequent low intensity contractions are a typical finding. Since the controller sets up a threshold to evaluate the onset of contraction, some of the low-intensity contractions below this threshold may not trigger the girdle pressure to increase. This will be similar situation of hypotonia. In this case, the use of the device may not cause any safety problem. Other discoordinate labor, Uterine hypertonus, may result from the constantly contracting state of some area in the myometrium. Extreme degree of this phenomenon is uterine fibrillation. In this case, the use of the device should be avoided.

4. Skewed contractions:
   A skewed contraction is characterized by a prolongation of the descending limb (relaxation phase) of the uterine contraction and is often seen in a mixed pattern with polysystole. The use of the inventive device implemented with a maximum duration at the target intrauterine pressure will not cause any problem.

5. Paired contractions:
   Paired contractions are a form of increased uterine contraction frequently characterized by one uterine contraction in close temporal relationship to a second uterine contraction, with the waveform returning to baseline between the two contractions. Usually, the second contraction is smaller in amplitude. Since the device sets the minimum interval between two cycles of girdle pressure increase, its use under this condition will not cause any safety problem.

6. Tachysystole:
   Tachysystole is defined as increased uterine contraction frequency. Because of the inevitable accompanying diminished or absent resting interval, decreased fetal oxygenation has been associated more often with this form of uterine hyperactivity than with increased intensity or duration of the uterine contraction. However, increased uterine activity of any type does not infer fetal stress or distress. Increased uterine activity may well be tolerated by some fetuses, whereas others may demonstrate stress even with uterine activity of a low intensity. As long as the fetus does not show distress, the use of the inventive device will not cause any problem. The software in device will diagnose the situation. However, a physician should make a final decision.

7. Tachysystole with progressive hypertonia:
   Progressive hypertonia, usually associated with tachysystole, is a form of uterine dysfunction. It represents incomplete relaxation between frequently occurring contractions. The software in the inventive device will diagnose the situation. However, a physician should make a final decision about continued use of the device.

8. Tachysystole with progression to tetany:
   Progressive uterine hypertonus, characterized as a rising baseline tone, is often accompanied by tachysystole. During the relaxation phase, the uterine tone does not completely return to the prior resting phase level before the next contraction begins. This may progress to tetany. The software in the inventive device will diagnose the situation. The use of the device should be decided by a physician under this circumstance.

9. Peaked contractions:
   A contraction pattern of high intensity and frequency, with a peaked contour, has been associated with preeclampsia and eclampsia. The software in the labor assisting device will diagnose the situation. The use of the device should be decided by a physician under this circumstance.

10. Hypersystole:

The amplitude of intensity is the pressure difference (in ramrig) between the peak of the uterine contraction and the uterine tone preceding the contraction. Hypersystole is defined as greater than 60 mmHg maximum pressure. Contractions of greater than 60 mmHg are seen with pharmacologically overstimulated or spontaneous abnormal labor. If there is enough uterine pressure, the use of the device is not necessary. A physician will make a decision on continuing the use of the device.

The childbirth assisting device of the present invention effectively prevents prolonged duration of labor and dystocia due to systemic analgesia, epidural anesthesia, or maternal exhaustion, leading to reduction of the cesarean section rate and rate of instrumental delivery. Since weakening of the secondary labor force is particularly common in patients receiving epidural anesthesia, the device can effectively prevent weakening of the secondary labor force under anesthesia, enabling a safer and less painful delivery. The inventive device includes means for analyzing the contraction curve and period in order to identify the presence of abnormal conditions, providing further safety benefits.

By reinforcing the secondary labor force, the childbirth assisting device can further reduce the rate of cesarean section associated with dystocia and also lower the dosage of oxytocin. Functioning through different mechanisms, the device can be used to complement the benefits of oxytocin in clinical practice.

it will be evident that there are additional embodiments and applications which are not disclosed in the detailed description but which clearly fall within the scope and spirit of the present invention. The specification is, therefore, not intended to be limiting, and the scope of the invention is to be limited only by the following claims.

We claim:

1. A system for assisting in childbirth comprising:
   a girdle having at least one inflatable bladder adapted to be positioned over a patient's abdomen for applying pressure to the abdomen;
   an air source for providing air for inflating said inflatable bladder;
   an intrauterine pressure monitor for generating an electrical signal indicative of the patient's contractions;
   an automatic controller means in electrical communication with said intrauterine pressure monitor for controlling the inflation and deflation of said at least one inflatable bladder in response to said electrical signal wherein the pressure is increased to a target intrauterine pressure at the onset of a contraction and decreased after the contraction is over, said automatic controller means having means for receiving and controlling air from said air source for inflating said inflatable bladder; and
   tubing having a first end attached to said girdle and a second end attached to said automatic controller means for conducting air between said girdle and said automatic controller means.

2. A system as in claim 1 wherein said intrauterine pressure monitor is external to the patient.

3. A system as in claim 1 wherein said intrauterine pressure monitor is internal to the patient.

4. A system as in claim 1 wherein the target intrauterine pressure is 40 to 60 mmHg during a first stage of labor with cervical dilation from 3 cm to 8 cm.

5. A system as in claim 1 wherein the target intrauterine pressure is 60 to 80 mmHg during a first stage of labor with cervical dilation from 8 cm to 10 cm.

6. A system as in claim 1 wherein the target intrauterine pressure is within the range of 80 to 160 mmHg during a second stage of labor.

7. A system as in claim 1 wherein a maximum girdle pressure is 150 mmHg during a first stage of labor with cervical dilation from 3 cm to 8 cm.

8. A system as in claim 1 wherein a maximum girdle pressure is 250 mmHg during a first stage of labor with cervical dilation from 8 cm to 10 cm.

9. A system as in claim 1 wherein a maximum girdle pressure is 350 mmHg during a second stage of labor.

10. A system as in claim 1 wherein said automatic controller means further generates an alarm signal in response to detection of a girdle pressure exceeding a maximum girdle pressure and further comprising:
    an alarm means triggered by said alarm signal; and
    valve means responsive to said alarm signal for deflating said girdle.

11. A system as in claim 1 wherein said automatic controller means includes timing means for limiting a duration of said pressure.

12. A system as in claim 1 wherein said automatic controller means further comprises:
    a memory means for storing a library of abnormal labor indicators; and
    a comparison means for comparing said electrical signal against said library of abnormal labor indicators to identify the presence of an abnormal labor condition.

* * * * *